US005684010A

United States Patent [19]

Schinazi

[11] Patent Number: 5,684,010
[45] Date of Patent: Nov. 4, 1997

[54] ENANTIOMERICALLY PURE β-D-DIOXOLANE NUCLEOSIDES WITH SELECTIVE ANTI-HEPATITIS B VIRUS ACTIVITY

[75] Inventor: Raymond F. Schinazi, Decatur, Ga.

[73] Assignee: Emory University, Atlanta, Ga.

[21] Appl. No.: 471,533

[22] Filed: Jun. 6, 1995

Related U.S. Application Data

[60] Division of Ser. No. 967,460, Oct. 28, 1992, Pat. No. 5,444,063, which is a continuation-in-part of Ser. No. 935,515, Aug. 25, 1992, which is a continuation-in-part of Ser. No. 622,762, Dec. 5, 1990, Pat. No. 5,179,104.

[51] Int. Cl.$^6$ .............. A61K 31/52; C07D 473/40; C07D 473/30; C07D 473/16
[52] U.S. Cl. .............. 514/266; 514/262; 544/244; 544/276; 544/297
[58] Field of Search .............. 544/244, 276, 544/277; 514/262, 266

[56] References Cited

U.S. PATENT DOCUMENTS

| | | | |
|---|---|---|---|
| 3,116,282 | 12/1963 | Hunter | 528/337 |
| 4,000,137 | 12/1976 | Dvonoch et al. | 544/277 |
| 4,140,761 | 2/1979 | Gerin et al. | 424/85 |
| 4,336,381 | 6/1982 | Nagata et al. | 544/313 |
| 4,861,759 | 8/1989 | Mitsuya et al. | 514/46 |
| 4,879,277 | 11/1989 | Mitsuya et al. | 514/49 |
| 4,880,784 | 11/1989 | Robins et al. | 514/48 |
| 4,916,122 | 4/1990 | Chu et al. | 514/50 |
| 4,963,533 | 10/1990 | de Clercq et al. | 514/49 |
| 4,968,674 | 11/1990 | Taniyama et al. | 514/63 |
| 5,011,774 | 4/1991 | Farina | 435/87 |
| 5,041,449 | 8/1991 | Belleau et al. | 514/274 |
| 5,047,407 | 9/1991 | Belleau et al. | 544/274 |
| 5,059,690 | 10/1991 | Zahler et al. | 544/276 |
| 5,089,500 | 2/1992 | Daluge | 514/261 |
| 5,122,517 | 6/1992 | Vince et al. | 514/50 |
| 5,151,426 | 9/1992 | Belleau et al. | 514/262 |
| 5,179,104 | 1/1993 | Chu et al. | 544/310 |
| 5,185,437 | 2/1993 | Koszalka et al. | 536/27.14 |
| 5,204,466 | 4/1993 | Liotta et al. | 544/317 |
| 5,210,085 | 5/1993 | Liotta et al. | 514/274 |
| 5,215,971 | 6/1993 | Datema et al. | 514/49 |
| 5,234,913 | 8/1993 | Furman, Jr. et al. | 514/49 |
| 5,246,924 | 9/1993 | Fox et al. | 514/50 |
| 5,248,776 | 9/1993 | Chu et al. | 544/310 |
| 5,270,315 | 12/1993 | Belleau et al. | 514/262 |
| 5,276,151 | 1/1994 | Liotta | 544/317 |
| 5,409,906 | 4/1995 | Datema et al. | 514/49 |
| 5,432,165 | 7/1995 | Adair et al. | 514/50 |
| 5,444,063 | 8/1995 | Schinazi | 514/262 |
| 5,446,029 | 8/1995 | Eriksson et al. | 514/45 |
| 5,466,806 | 11/1995 | Belleau et al. | 544/310 |
| 5,486,520 | 1/1996 | Belleau et al. | 514/274 |
| 5,532,246 | 7/1996 | Belleau et al. | 514/274 |
| 5,539,116 | 7/1996 | Liotta et al. | 544/317 |

FOREIGN PATENT DOCUMENTS

| | | |
|---|---|---|
| 0 206 497 | 12/1986 | European Pat. Off. . |
| 0 217 580 | 4/1987 | European Pat. Off. . |
| 0 337 713 | 10/1989 | European Pat. Off. . |
| 0 433 898 | 12/1989 | European Pat. Off. . |
| 0 361 831 | 4/1990 | European Pat. Off. . |
| 0 375 329 | 6/1990 | European Pat. Off. . |
| 0 382 526 | 8/1990 | European Pat. Off. . |
| 0 494 119 | 7/1992 | European Pat. Off. . |
| 0 515 144 | 11/1992 | European Pat. Off. . |
| 0 515 156 | 11/1992 | European Pat. Off. . |
| 0 515 157 | 11/1992 | European Pat. Off. . |
| 0 526 253 | 2/1993 | European Pat. Off. . |
| WO90/12023 | 10/1990 | WIPO . |
| WO91/11186 | 8/1991 | WIPO . |
| WO91/17159 | 11/1991 | WIPO . |
| WO92/01393 | 1/1992 | WIPO . |
| WO92/06102 | 4/1992 | WIPO . |
| WO92/08717 | 5/1992 | WIPO . |
| WO92/10496 | 6/1992 | WIPO . |
| WO92/10497 | 6/1992 | WIPO . |
| WO92/14729 | 9/1992 | WIPO . |
| WO92/14743 | 9/1992 | WIPO . |
| WO92/15308 | 9/1992 | WIPO . |
| WO92/18517 | 10/1992 | WIPO . |
| WO92/21676 | 12/1992 | WIPO . |
| WO94/04154 | 3/1994 | WIPO . |
| WO94/09793 | 5/1994 | WIPO . |
| WO94/14456 | 7/1994 | WIPO . |
| WO94/1802 | 7/1994 | WIPO . |
| WO94/27616 | 12/1994 | WIPO . |
| WO95/07086 | 3/1995 | WIPO . |
| WO95/07287 | 3/1995 | WIPO . |
| WO95/20595 | 8/1995 | WIPO . |

OTHER PUBLICATIONS

Acton, et al., "Improved Antitumor Effects in 3'–Branched Homologues of 2'–Deoxythioguanosine. Synthesis and Evaluation of Thioguanine Nucleosides of 2,3–Dideoxy–3–(hydroxymethyl)–D–erythro–pentofuranose," *J. Med. Chem.* 22:518–525 (1979).

(List continued on next page.)

*Primary Examiner*—Johann Richter
*Assistant Examiner*—Laura R. Cross
*Attorney, Agent, or Firm*—Sherry M. Knowles, Esq.; King & Spalding

[57] ABSTRACT

A method and composition for the treatment of humans infected with HBV that includes the administration of an HBV treatment amount of a β-dioxolanyl purine nucleoside of the formula:

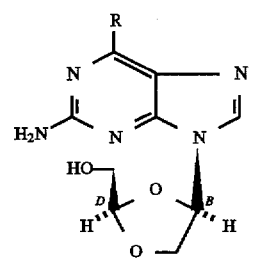

wherein R is OH, Cl, $NH_2$, or H, or a pharmaceutically acceptable salt or derivative of the compound, optionally in a pharmaceutically acceptable carrier or diluent.

40 Claims, 1 Drawing Sheet

OTHER PUBLICATIONS

Ayoola, et al., "Progress in the Control of Viral Hepatitis. Memorandum from a WHO Meeting," *Bulletin of the World Health Organization*, 66(4):443–455 (1988).

Balzarini, J., et al., "Potent and Selective Anti–HTLV–III/LAV Activity of 2',3'–Dideoxycytidinene . . . ," *Bioch. and Bioph. Res. Comm.* 140(2):735–742 (1986).

Bamford, et al., "Synthesis and Antiviral Activity of 3'–Deoxy–3'–C–hydroxymethyl Nucleosides," *J. Med. Chem.*, 33:2494–2501 (1990).

Beach, J.W., et al., "Synthesis of EnantiomericallyPure (2'R,5'S)–(–)–1–[2–(hydroxymethyl)–oathiolan–5–yl]Cytosine . . . ," *J. Org. Chem.* 57:2217–2219 (1992).

Beasley, et al., "Hepatocellular Carcinoma and Hepatitis B Virus," *The Lancet*, 1129–1133 (1981).

Belleau, B., et al., "Design and Activity of a Novel Class of Nucleoside Analogs . . . ," *Intl. Conf. on AIDS*, Montreal, Quebec, Canada, Jun. 4–9, 1989.

Borthwick, D.A., et al., "Synthesis and Enzymatic Resolution of Carbocyclic 2'–Ara–Fluoro–Guanosine: A Potent New Anti–Herpetic Agent," *J. Chem. Soc. Commun.*, 10:656–658 (1988).

Boutelje, et al., *Chemical Abstracts* 108:128048 (1987).

Carter, et al., "Activities of (–)–Carbovir and 3'–Azido–3'–Deoxythymidine Against Human Immunodeficiency Virus In Vitro," *Antimicorbial Agents and Chemotherapy*, 34(6):1297–1300 (1990).

Chang, C.–N., et al., "Biochemical Pharmacology of (+) and (–)–2',3'–Dideoxy–3'Thioacytidine as Anti–Hepatatis B Virus Agents," *J. Biol. Chem.* 267(31):22414–22420 (1992).

Chang, Chien–Neng, et al., "Deoxycytidine Deaminase–resistant Steroisomer is the Active Form of (+)–2',3'–Thiacytidine in the Inhibition of Hepatitis B Virus Replication," *J. Bio. Chem.*, 267(20):13938–13942 (1992).

Chang, Chungming, et al., "Production of Hepatitis B Virus in vitro by Transient Expression . . .," *The EMBO J.* 6(3):675–680 (1987).

Chen, Chin–Ho, et al., "Delayed Cytotoxicity and Selective Loss of Mitochondrial DNA in Cells . . . ," *J. Bio. Chem.* 264(20):11934–11937 (1989).

Cheng, Y.C., et al., "Human Deoxycytidine Kinase Purification and Characterization . . .," *Biochim. Biophys. Acta.* 481:481–492 (1977).

Cheng, et al., *J. Biol. Chem.*, 262:2187 (1987).

Chu, et al., "Structure–Activity Relationships of Pyrimide Nucleosides as Antiviral Agents for Human Immunodeficiency Virus Type 1 in Peripheral Blood Mononuclear Cells," *J. Med. Chem.*, 32:612 (1989).

Chu, et al., "Enantiomeric Synthesis of (+)–BCH–189[(+)–(2S,5R)–1–[2–(Hydroxymethyl)–1,3–oxathiolane–5–yl]cytosine] from D–Mannose and Its Anti–HIV Activity," *J. Org. Chem.*, 56:6503–6505 (1991).

Chu, C.K., et al., "An Efficient Total Synthesis of 3'–Azido–3'–Deoxythimidine (AZT) and 3'–Azido–2',3'–Dideoxyuridine (AZDDU, CS–87) from D–Mannitol," *Tetrahedron Lett*, 29(42):5349–5352 (1988).

Chu, et al., "Comparative Activity of 2',3'–Saturated and Unsaturated Pyrimidine and Purine Nucelosides . . . , " *Biochem. Pharm.* 37(19):3543–3548 (1988).

Chu, et al., "Structure–Activity Relationships of Pyrimidine Nucleosides as Antiviral Agents . . . , " *J. Med. Chem.* 32:612–617 (1989).

Chu, C.K., et al., "2'–Fluoro–5–Methylβ–L–Arabinofuranocyluracil as a Novel Antiviral Agent for Hepatitis B . . . , " *Antimicrob. Agents Chemother.*, 39(4):979–981 (1995).

Chu, et al., "Synthesis and Biological Evaluation of D–(2S) and L–(2R)–1,3–Oxathiolanyl–and D–(2R)–and L–(2S)–1,3–Dioxolanyl–Nucleosides as Anti–HIV and Anti–HBV Agents,"0 *Antiviral Research*, 30(S1):192 (Apr. 1993).

Chu, et al., "Synthesis and Anti–HIV and Anti–HBV Activity of Enantiomerically Pure Oxathiolane Nucleosides," *Antiviral Research*, 17(S1):2 (Mar. 1992).

Chu, et al., "Asymmetric Synthesis of Enantiomerically Pure (–)–(1'R,4'R)–Dioxolane–thymine and Its Anti–HIV Activity," *Tetrahedron Letters*, 32(31):3791–3794 (1991).

Coates, J., et al., "The Separated Enaniomers of 2'–deoxy–3'–thiacytidine (BCH–189) Both Inhibit Human Immunodeficiency Virus Replication In Vitro," *Antimicrob. Agents Chemother.* 36(1):202–205 (1992).

Condreay, et al., "Evaluation of the Potent Anti–Hepatitis B Virus Agent (–) cis–5–Fluoro–1–[2–(Hydroxymethyl)–1,3–Oxathiolan–5–yl]Cytosine in a Novel In Vivo Model," *Antimicrobial Agents and Chemotherapy*, 616–619 (1992).

Cretton, E., et al., "Catabolism of 3'–Azido–3'–Deoxythymidine in Heptaocytes and Liver Microsomes, with Evidence of Formation of 3'Amino–3'–Deoxythymidine a Highly Toxic Catabolite for Human Bone Marrow Cells," *Molecular Pharmacology*, 39:258–266 (1991).

Cretton, E., et al., "Pharmokinetics of 3'–Azido–3'–Dexoythymidine and its Catabolites and Interactions with Probenecid in Rhesus Monkeys," *Antimicrobial Agents and Chemotherapy*, 35(5):801–807 (1991).

Di Bisceglie, Adrian M. Rustgi, Vinod K. et al., "Hepatocellular Carcinoma," NIH Conference, *Annals of Internal Medicine*, 108:390–401 (1988).

Doong, Shin–Lian, et al., "Inhibition of the Replication of Heptitis B virus in vitro by 2',3'–Dideoxy–3'–Thiacytidine and Related Analogues," *Natl. Acad. Sci. USA*, 88:8495–8499 (1991).

Eriksson, et al. *Antimicrobial Agents and Chemotherapy*, 33(10):1729–1734 (1988).

Frick, et al., "Pharmacokinetics, Oral Bioavailability, and Metabolic Disposition in Rats of (–)–cis–5–Fluoro–1 [2–(Hydroxymethyl)–1,3–Oxzathiolan–5–yl]Cytosine, a Nucleoside Analog Active against Human Immunodeficiency Virus and Hepatitis B Virus," *Antimicrobial Agents and Chemotherapy*, 37(11):2285–2292 (1993).

Furman, et al., "The Anti–Hepatitis B Virus Activities, Cytotoxicities, and Anabolic Profiles of the (–) and (+) Enantiomers of cis–5–Fluoro–1–[2–(Hydromethyl)–1,3–Oxathiolane–5–yl)] Cytosine," *Antim. Agents and Chemo.*, 36(12):2686–2692 (1992).

Furman, et al., *Proc. Natl. Acad. Sci. U.S.A.*, 83:3333 (1986).

Ganem, "Animal Models of Hepatitis B Virus," *Experimental Models in Antimicrobial Chemotherapy*, 2:259–272 (1986).

Ganem, Don et al., "The Molecular Biology of the Hepatitis B Viruses," *Ann. Rev. Biochem.* 56:651–693 (1987).

Gerlt, *Chemical Abstracts*, 107:14979 (1987).

Hamamoto, et al., *Antimicrobl. Agents. Chemother.*, 31:907 (1987).

Herdewign, P. et al., "Resolution of Aristeromycin Enantiomers," *J. Med. Chem.*, 28:1385–1386 (1985).

Hoong, et al., "Enzyme–Mediated Enantioselective Preparation of Pure Enantiomers of the Antiviral Agent 2',3'–Dideoxy–5–Fluoro–3'–Thiacytidine (FTC) and Related Compounds," *J. of Org. Chem.*, 57:5563–5565 (1992).

Jeong, L., et al., "Asymmetric Synthesis and Biological Evaluation of β–L–(2R,5S)–and a–L–(2R–5R)–1,3–Oxathiolane–Pyrimidine and –Purine Nucleotsides and Potential Anti–HIV Agents," *J. Med. Chem.*, 36(2):181–195 (1993).

Jeong, et al., "An Efficient Synthesis of Enantiomerically Pure (+)–(2S,5R)–1–[2–(Hydroxymethyl)–1,–oxathiolan–5–y;]cytosine [(+)–BCH–189] from D–Galactose," *Tetrahedron Letters*, 33(5):595–598 (1992).

Jones and Bischofberger, "Minireview: nucleotide prodrugs," *Antiviral Research*, 27:1–17 (1995).

Jurovcik and Holy, "Metabolism of pyrimidine L–nucleosides," *Nucleic Acid Research*, 3(8):2143–2154 (1976).

Kassianides, Chris, et al., "Inhibition of Duck Hepatitis B Virus Replication by 2',3'–Dideoxycytidine," *Gastroenterology*, 97(5):1275–1280 (1989).

Kim, H.O., et al., "Potent Anti–HIV and Anti–HBV Activities of (–)–L–β–Dioxolane–C and (+)–L–β–Dioxolane–T and Their Asymmetric Syntheses," *Tetrahedron Lett*, 33(46):6899–6902 (1992).

Kim, H.O., et al., "L–β–(2S,4S)–and L–α–(2S,4R)–Dioxolanyl Nucleosides as Potential Anti–HIV Agents: Asymmetric Synthesis and Structure–Activity Relationships," *J. Med. Chem.*, 36(5):519–528 (1993).

Kim, et al., "L–β–(2S,4S)–and L–α–(2S,4R)–Dioxolanyl Nucleosides as Potential Anti–HIV Agents: Asymmetric Synthesis and Structure–Activity Relationships," *J. of Med. Chem.*, 36(5):519–528 (1993).

Krenitsky, T.A. et al., "An Enzymatic Synthesis of Purine D–arabinonucleosides," *Carbohydrate Research*, 97:139–146 (1981).

Lee, Bonita, et al., "In Vitro and In Vivo Comparison of the Abilities of Purine and Pyrimidine 2',3'–Dideoxynucleosides To Inhibit Duck Hepadnavirus," *Antimicrobial Agents and Chemotherapy*, 33(3):336–339 (1989).

Lin, et al., "Potent and Selective In Vitro Activity of 3'–Deoxythminidine–2–Ene–(3'–Deoxy–2',3'–Didehydrothymidine) Against Human Immunodeficiency Virus," *Biochem. Pharm.*, 36(17):2716 (1987).

Mahmoudian, M., et al., "Enzymatic Production of Optically Pure (2'R–cis)–2;–deoxy–3'–tiacytidine (3TC, Lamivudine): A Potent Anti–HIV Agent," published by the Glaxo Group Research Ltd., *Enzyme Microbl. Technol.*, 15:749–755 (1993).

Martin, et al., *J. Med. Chem.*, 33:2137 (1990).

Matthes, E., et al., "Potent Inhibition of Hepatitis B Virus Production In Vitro by Modified . . . ," *Anti. Agents and Chemot*, 34(10):1986–1990 (1990).

Miller, Roger H., et al., "Common Evolutionary Origin of Hepatitis B Virus and Retroviruses," *Proc. Natl. Acad. Sci. USA*, 83:2531–2535 (1986).

Mitsuya, H., et al., "3'–Azido–3'–Deoxythymidine (BW A 509U): An Antiviral Agent that Inhibits and Infectivity and Cytopathic Effect of Human T–Lymphotropic Virus Type III/Lymphadenopathy–Associated Virus In Vitro," *Proc. Natl. Acad. Sci., USA* 82:7097–7100 (1985).

Mitsuya, H., et al., "Rapid in Vitro Systems for Assessing . . . ," *AIDS: Modern Concepts and Therapeutic Challenges*, S. Broder, Ed. p. 303, Marcel–Dekker, New York (1987).

Mitsuya, H., et al., "Molecular Targets for AIDS Therapy," *Science*, 249:1533–1544 (1990).

Norbeck, D., et al. "A New 2',3'–Dideoxynucleoside Prototype with In Vitro Activity Against HIV," *Tetrahedron Lett*, pp. 6263–6266 (1989).

Norin, *Chemical Abstracts*, 108:146380 (1987).

Ohno, et al., *Chemocal Abstracts*, 112:194612 (1989).

Okabe, M., et al., "Synthesis of the Dideoxynucleosides ddC and CNT . . . ," *J. Org. Chem.*, 53(20):4780–4786 (1988).

Pai, S.b., et al., "Inhibition of Hepatitis B Virus by a Novel L–Nucleoside, 2'–Fluoro–5–Methyl–β–L–Arabinofuranosyl Uracil," *Antimicrobial Agents and Chemotheraphy*, 40(2):380–386 (1996).

Paff, et al., "Intracellular Metabolism of (–)–and (+)–cis–5–Fluoro–1–[2–(Hydroxymethyl)–1, 3–Oxathiolan–5–yl]Cytosine in HepG2 Derivative 2.2.15 (Subclone P5A) Cells," *Antimicrobial Agents and Chemotherapy*, 1230–1238 (1994).

Richman, D. D., et al., "The Toxicity of Azidothymidine (AZT) in the Treatment of Patients with AIDS . . . , " *N. Eng. J. Med.*, 317(4):192–197 (1987).

Saari, et al., "Synthesis and Evaluation of 2–Pyridinone Derivatives as HIV–1–Specific Reverse Transcriptase Inhibitors. 2. Analogues of 3–Aminopyridin–2(1H)–one," *J. Med. Chem.*, 35:3792–3802 (1992).

Satsumabayashi, S. et al., "The Synthesis of 1,3–Oxathiolane–5–one Derivatives," *Bull. Chem. Soc. Japan*, 45:913–915 (1972).

Schinazi, et al., "Pure Nucleoside Enantiomers of β–2', 3'–Dideoxycytidine Analogs are Selective Inhibitors of Hepatitis B Virus In Vitro," *Antimicrobial Agents and Chemotherapy*, 38(9):2172–2174 (1994).

Schinazi, R.F., et al., "Selective Inhibition of Human Immunodeficiency Viruses by Racemates and Enantiomers of cis–5–Fluoro–1–2–(Hydroxymethyl)–1, 3–Oxathiolan–5–yl) Cytosine," *Antim. Agents and Chemo.*, 36(11):2423–2431 (1992).

Schinazi, R.F., et al., "Rapid Communications: Substrate Specificity of *Escherichia Coli*. Thymidine Phosphorylase for Pyrimidine Nucleoside with an Anti–Human Immunodeficiency Virus Activity," *Bioch. Pharm.*, 44(2):199–204 (1992)*.

Schinazi, R.F., et al., "Activities of the Four Optical Isomers of 2'3'–Dideoxy–3'–Thiacytidine . . . ," *Antimic. Agents & Chemo.*, 36(3):672–676 (1992)*.

Schinazi, R.F., et al., "Insights into HIV Chemotherapy," *AIDS Research and Human Retroviruses* 8(6):963–989 (1992).

Schinazi, R.F., et al., "Pharmacokinetics and Metabolism of Racemic 2',3'–Dideoxy–5 . . . ," *Antimicrobial Agents and Chemotherapy* 36(11):2432–2438 (1992).

Schinazi, et al., *Antimicrob. Agents Chemother.*, 33:115 (1989).

Secrist, J.A., et al., "Resolution of Racemic Carbocyclic Analogues of Purine Nucleosides Through the Action of Adenosine Deaminase Antiviral Activity of the Carbocyclic 2'–Deoxyguanosine," *J. Med. chem.*, 30:746–749 (1987).

Sells, Mary Ann, et al, "Production of Hepatitis B Virus Particles in Hep G2 Cells . . . , " *Proc. Natl. Acad. Sci. USA*, 84:1005–1009 (1987).

Shuto, et al., "Phospholipase D–Catalyzed Trans–Alkylphosphorylation; A Facile One–Step Synthesis of Nucleoside 5'–Alkylphosphates," *Chem. Pharm. Bull.*, 36:5020 (1988).

Soudeyns, H., et al., "Anti–Human Immunodeficiency Virus Type 1 Activity and In Vitro Toxicity of 2'–Deoxy–3'–Thiacytidine . . ., " *Antimicrobial Agents and Chemotherapy*, 35(7):1386–1390 (1991).

Spadari, S., et al., "L–Thymidine Is Phosphorylated by Herpes Simplex Virus Type 1 . . . , " *J. Med. Chem.*, 35(22):4214–4220 (1992).

St. Clair et al., *Antimicrob. Agents Chemother.*, 31:1972 (1987).

Sterzycki, R.Z., et al., "Synthesis and Anti–HIV Activity of Several 2'–Fluoro–Containing Pyrimidine Nucelosides," *J. Med. Chem.*, 33(8):2150–2157 (1990).

Storer, R., et al., "The Resolution and Absolute Stereochemistry of the enantiomeris of cis–1–2–(Hydromethyl)–1, 3–Oxathiolan–5–yl)cytosine (BCH–189); Equipotent Anti–HIV Agents," *Nucleosides & Nucleotides*, 12(2):225–236 (1993).

Van Roey, et al., *J. Am. Chem. Soc.*, 110:2277 (1988).

Van Roey, et al., *Proc. Natl. Acad. Sci. USA*, 86:3929 (1989).

Volk, Wesley A., editor, "Hepatitis," *Essentials of Medical Microbiology*, J.B. Lippincott Company, (Philadelphia/Toronto), 2nd Ed., pp. 609–618 (1982).

Vorbrüggen, et al., "Nucleoside Synthesis with Trimethylsilyl Triflate and Perchlorate as Catalysts," *Chem. Ber.*, 114:1234–1255 (1981).

Watanabe, et al., *J. Med. Chem.*, 33:2145 (1990).

Wilson, L.J., et al., "The Synthesis and Anti–HIV Activity of Pyrimidine Dioxolanyl Nucleosides," *Bioorganic & Medicinal Chemistry Letters*, 3(2):169–174 (1993).

Wilson, L.J., et al., "A General Method for Controlling Glycosylation Stereochemistry in the Synthesis . . ., " *Tetrahedron Lett*, 31(13):1815–1818 (1990).

Yarchoan, et al., *Science*, 245:412 (1989).

Yokota et al., "Comparative Activities of Several Nucleoside Analogs Against Duck . . . , " *Antimicrobial Agents and Chemotherapy*, 34(7):1326–1330 (1990).

Zhu, Zhou, et al., "Cellular Metabolism of 3'–Azido–2', 3'–Dideoxyuridine with Formation of 5'–O–Diphophoshexase . . . " *Molecular Pharmacology*, 38:929–938 (1990).

FIG. 1

Figure 1:
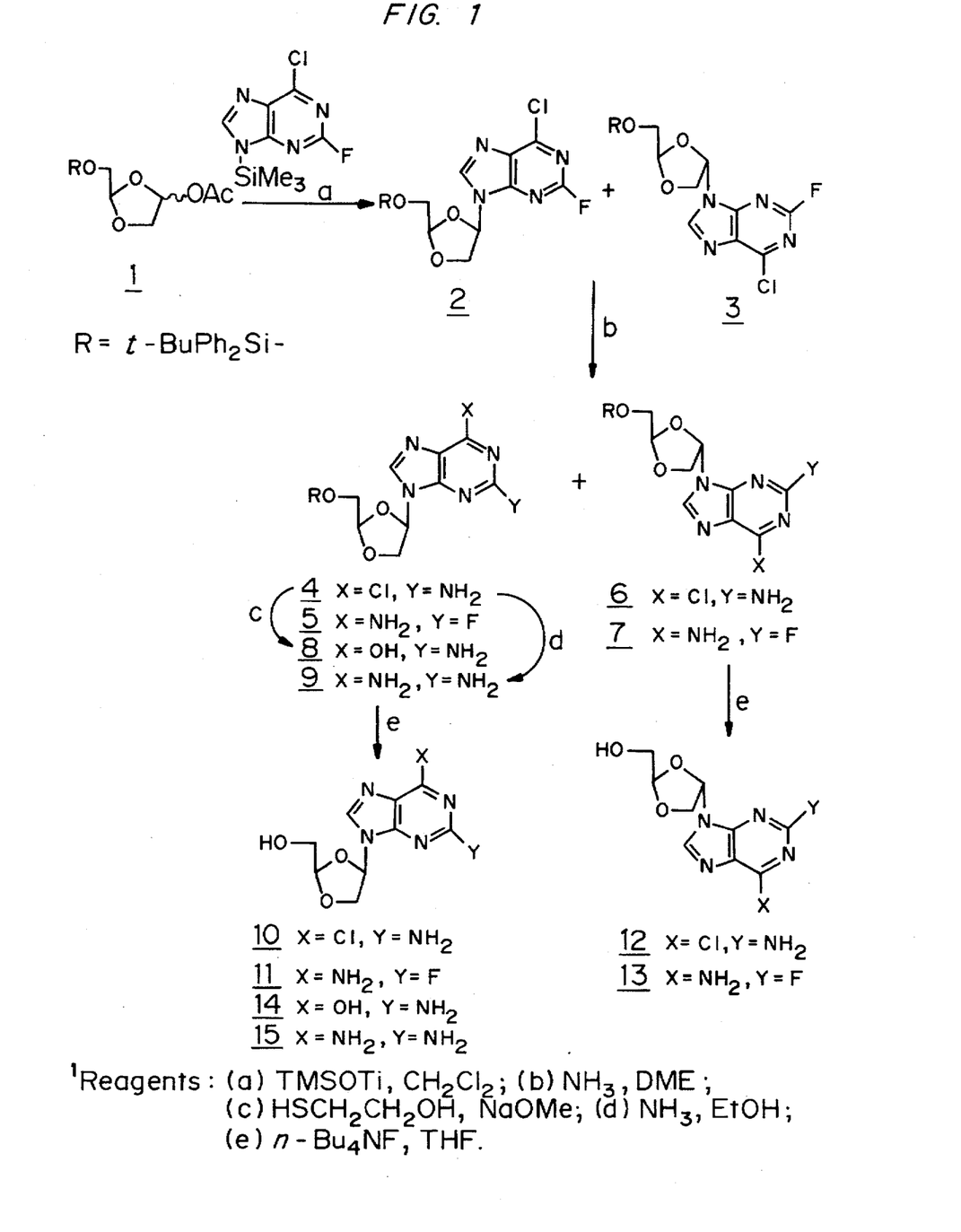
FIG. 1 is an illustration of the method of preparation of a variety of enantiomerically pure β-D-dioxolanyl purine nucleosides.

$^1$Reagents: (a) TMSOTf, $CH_2Cl_2$; (b) $NH_3$, DME; (c) $HSCH_2CH_2OH$, NaOMe; (d) $NH_3$, EtOH; (e) $n\text{-}Bu_4NF$, THF.

ENANTIOMERICALLY PURE β-D-DIOXOLANE NUCLEOSIDES WITH SELECTIVE ANTI-HEPATITIS B VIRUS ACTIVITY

This application is a divisional of U.S. Ser. No. 07/967,460 filed on Oct. 28, 1992 (now U.S. Pat. No. 5,444,063), which is a continuation-in-part of U.S. Ser. No. 07/935,515 filed on Aug. 25, 1992, which is a continuation-in-part of U.S. Ser. No. 622,762 filed on Dec. 5, 1990 (now U.S. Pat. No. 5,179,104).

BACKGROUND OF THE INVENTION

This invention is in the area of methods for the treatment of hepatitis B virus (also referred to as "HBV") that includes administering an effective amount of one or more of the active compounds disclosed herein, or a pharmaceutically acceptable derivative or prodrug of one of these compounds.

HBV is second only to tobacco as a cause of human cancer. The mechanism by which HBV induces cancer is unknown, although it is postulated that it may directly trigger tumor development, or indirectly trigger tumor development through chronic inflammation, cirrhosis, and cell regeneration associated with the infection.

Hepatitis B virus has reached epidemic levels worldwide. After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed.

Patients typically recover from acute viral hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is in fact very similar to that of acquired immunodeficiency syndrome, which accounts for why HBV infection is common among patients with AIDS or HIV-associated infections. However, HBV is more contagious than HIV.

A human serum-derived vaccine has been developed to immunize patients against HBV. Vaccines have been produced through genetic engineering. While the vaccine has been found effective, production of the vaccine is troublesome because the supply of human serum from chronic carriers is limited, and the purification procedure is long and expensive. Further, each batch of vaccine prepared from different serum must be tested in chimpanzees to ensure safety. In addition, the vaccine does not help the patients already infected with the virus.

Daily treatments with α-interferon, a genetically engineered protein, has also shown promise. However, to date there is no known pharmaceutical agent that effectively inhibits the replication of the virus in humans.

In light of the fact that hepatitis B virus has reached epidemic levels worldwide, and has severe and often tragic effects on the infected patient, there remains a strong need to provide new effective pharmaceutical agents to treat humans infected with the virus that have low toxicity to the host.

Therefore, it is another object of the present invention to provide a method and composition for the treatment of human patients or other hosts infected with HBV.

SUMMARY OF THE INVENTION

In a preferred embodiment, the invention is a method for the treatment of humans infected with HBV that includes administering an HBV treatment amount of an enantiomerically pure β-D-dioxolanyl purine nucleoside of the formula:

wherein R is OH, Cl, $NH_2$, or H, or a pharmaceutically acceptable salt or derivative of the compound, optionally in a pharmaceutically acceptable carrier or diluent. The compound wherein R is chloro is referred to as (−)-(2R,4R)-2-amino-6-chloro-9-[(2-hydroxymethyl)-1,3-dioxolan-4-yl] purine. The compound wherein R is hydroxy is (−)-(2R,4R)-9-[(2-hydroxymethyl)-1,3-dioxolan-4-yl] guanine. The compound wherein R is amino is (−)-(2R,4R)-2-amino-9-[(2-hydroxymethyl)-1,3-dioxolan-4-yl] adenine. The compound wherein R is hydrogen is (−)-(2R,4R)-2-amino-9-[(2-hydroxymethyl)-1,3-dioxolan-4-yl] purine. The absolute configuration of these compounds has not been determined by crystallography. Designations are based on comparision of the structure to the configuration of the parent sugar used to make the compound.

In another embodiment, an effective amount of the β-L-dioxolanyl purine nucleoside enantiomer, or a racemic mixture of the β-L- and β-D-dioxolanyl purine nucleoside is administered to the patient.

The disclosed β-dioxolane purine nucleosides, or their pharmaceutically acceptable derivatives or salts or pharmaceutically acceptable formulations containing these compounds are useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

In another embodiment, the invention includes a method for the treatment of humans infected with HBV that includes administering an HBV treatment amount of a prodrug of the specifically disclosed enantiomerically pure β-D-dioxolanyl purine nucleosides. A prodrug, as used herein, refers to a pharmaceutically acceptable derivative of the specifically disclosed nucleoside, that is converted into the nucleoside on administration in vivo, or that has activity in itself. Nonlimiting examples are pharmaceutically acceptable salts (alternatively referred to as "physiologically acceptable salts"), and the 5' and $N^6$ acylated or alkylated derivatives of the active compound (alternatively referred to as "physiologically or pharmaceutically acceptable derivatives"). In one embodiment, the acyl group is a carboxylic acid ester in which the non-carbonyl moiety of the ester group is selected from straight, branched, or cyclic $C_1$–$C_{20}$ alkyl; alkoxyalkyl including methoxymethyl; aralkyl including benzyl; aryloxyalkyl such as phenoxymethyl; aryl including phenyl optionally substituted with halogen, $C_1$ to $C_4$ alkyl or $C_1$ to $C_4$ alkoxy; a dicarboxylic acid such as succinic acid; sulfonate esters such as alkyl or aralkyl sulphonyl including methanesulfonyl; and the mono, di and triphosphate esters.

As used herein, the term alkyl specifically includes but is not limited to methyl, ethyl, propyl, butyl, pentyl, hexyl, isopropyl, isobutyl, sec-butyl, t-butyl, isopentyl, amyl, t-pentyl, cyclopentyl, and cyclohexyl. As used herein, the term acyl specifically includes but is not limited to acetyl, propionyl, butyryl, pentanoyl, 3-methylbutyryl, hydrogen succinate, 3-chlorobenzoate, benzoyl, acetyl, pivaloyl, mesylate, propionyl, valeryl, caproic, caprylic, capric, lauric, myristic, palmitic, stearic, and oleic. The nucleoside can also be provided as a 5' ether lipid, as disclosed in the following references, which are incorporated by reference herein: Kucera, L. S., N. Iyer, E. Leake, A. Raben, Modest E. J., D. L. W., and C. Piantadosi. 1990. Novel membrane-interactive ether lipid analogs that inhibit infectious HIV-1 production and induce defective virus formation. AIDS Res Hum Retroviruses. 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. Synthesis and evaluation of novel ether lipid nucleoside conjugates for anti-HIV activity. J Med Chem. 34:1408–1414; Hostetler, K. Y., D. D. Richman, D. A. Carson, L. M. Stuhmiller, G. M. T. van Wijk, and H. van den Bosch. 1992. Greatly enhanced inhibition of human immunodeficiency virus type 1 replication in CEM and HT4-6C cells by 3' -deoxythymidine diphosphate dimyristoylglycerol, a lipid prodrug of 3'-deoxythymidine. Antimicrob Agents Chemother. 36:2025–2029; Hostetler, K. Y., L. M. Stuhmiller, H. B. Lenting, H. van den Bosch, and D. D. Richman. 1990. Synthesis and antiretroviral activity of phospholipid analogs of azidothymidine and other antiviral nucleosides. J. Biol Chem. 265:6112–7.

The β-dioxolanyl purine nucleoside can be converted into a pharmaceutically acceptable ester by reaction with an appropriate esterifying agent, for example, an acid halide or anhydride. The nucleoside or its pharmaceutically acceptable derivative can be converted into a pharmaceutically acceptable salt thereof in a conventional manner, for example, by treatment with an appropriate base. The ester or salt can be converted into the parent nucleoside, for example, by hydrolysis.

The active compound can be provided in the form of pharmaceutically acceptable salts. As used herein, the term pharmaceutically acceptable salts or complexes refers to salts or complexes of the nucleosides that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

Modifications of the active compound, specifically at the $N^6$ and 5'-0 positions, can affect the bioavailability and rate of metabolism of the active species, thus providing control over the delivery of the active species.

The active compound, or pharmaceutically acceptable derivative or salt thereof can also be mixed with other active materials that do not impair the desired action, or with materials that supplement the desired action, such as antibiotics, antifungals, antiinflammatories, or other antivirals, including anti-HBV or anti-HIV agents.

In one embodiment of the invention, one or more of the active compounds is administered in an alternative fashion with one or more other anti-HBV agents, to provide effective anti-HBV treatment. Examples of anti-HBV agents that can be used in alternation therapy include but are not limited to the (−)-enantiomer or racemic mixture of 2-hydroxymethyl-5-(5-fluorocytosin-1-yl)-1,3-oxathiolane ("FTC", see WO92/14743), its physiologically acceptable derivative, or physiologically acceptable salt; (−)-enantiomer or racemic mixture of 2-hydroxymethyl-5-(cytosin-1-yl)-1,3-oxathiolane (also referred to as "BCH-189" or 3TC, see EPA Publication No. 0 382 526), its physiologically acceptable derivative, or physiologically acceptable salt; an enantiomer or racemic mixture of 2'-fluoro-5-iodo-arabinosyluracil (FIAU); an enantiomer or racemic mixture of 2'-fluoro-5-ethyl-arabinosyluracil (FEAU); carbovir, or interferon.

Any method of alternation can be used that provides treatment to the patient. Nonlimiting examples of alternation patterns include 1–6 weeks of administration of an effective amount of one agent followed by 1–6 weeks of administration of an effective amount of a second anti-HBV agent. The alternation schedule can include periods of no treatment.

In another embodiment, the active compound or its derivative or salt can be administered in combination with another anti-HBV agent, including those listed above. In general, during alternation therapy, an effective dosage of each anti-HBV agent is administered serially, whereas in combination therapy, a reduced dosage of two or more anti-HBV agents are administered together. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

DETAILED DESCRIPTION OF THE INVENTION

As used herein, the term "enantiomerically pure" refers to a nucleoside composition that includes at least approximately 95%, and preferably 97%, of a single enantiomer of that nucleoside.

The invention as disclosed herein is a method and composition for the treatment of HBV infection, in humans or other host animals, that includes administering an effective amount of one or more of the above-identified compounds, or a physiologically acceptable derivative, including a 5' and or $N^6$ alkylated or acylated derivative, or a physiologically acceptable salt thereof, optionally in a pharmaceutically acceptable carrier. The compounds of this invention either possess anti-HBV activity, or are metabolized to a compound or compounds that exhibits antiretroviral activity.

I. Preparation of Enantiomerically Pure Dioxolane Nucleosides

Enantiomerically pure β-D-dioxolane-nucleosides can be prepared as disclosed in detail below, and as described in PCT/US91/09124. The process involves the initial preparation of (2R,4R)- and (2R,4S)-4-acetoxy-2-(protected-oxymethyl)-dioxolane from 1,6-anhydromannose, a sugar that contains all of the necessary stereochemistry for the enantiomerically pure final product, including the correct diastereomeric configuration about the 1 position of the sugar (that becomes the 4'-position in the later formed nucleoside).

The (2R,4R)- and (2R,4S)-4-acetoxy-2-(protected-oxymethyl)-dioxolane is condensed with a desired heterocyclic base in the presence of $SnCl_4$, other Lewis acid, or trimethylsilyl triflate in an organic solvent such as dichloroethane, acetonitrile, or methylene chloride, to provide the stereochemically pure dioxolane-nucleoside.

In preparing enantiomerically pure dioxolane nucleosides, care should be taken to avoid strong acidic conditions that would cleave the dioxolane ring. Reactions should be performed, if possible, in basic or neutral conditions, and when acidic conditions are necessary, the time of reaction should be minimized.

Racemic mixtures of dioxolane purine nucleosides can be prepared as described in EPA Publication No. 0 382 526. The β-L-enantiomer can be isolated from the racemic mixture by known methods, including through the use of a chiral HPLC column.

FIG. 1 and Example 1 set out a process for the preparation of the active compounds. The starting material, compound 1, is prepared as disclosed in PCT/US91/09124 (compound 8 in that application). 2,6-Disubstituted purine derivatives were synthesized by the condensation of acetate 1 with the silylated 6-chloro-2-fluoropurine, which gave a mixture (α/β=1/1.3) of 2 and 3. The initially formed $N^7$-isomer was again converted to the $N^9$-isomer during stirring overnight at room temperature. The analytical sample was obtained from the separation of α,β-mixture to the individual isomers 2 and 3 by a preparative TLC using $CH_2Cl_2$-acetone (19:1) as the developing solvents. However, for the purpose of preparing the final products 10–15, the mixture of 2 and 3 was treated with $NH_3$ in DME (Robins, M.J.; Vznanski, B. Nucleic acid related compounds. 34. Non-aqueous Diazotization with tert-Butyl nitrite. Introduction of fluorine, chlorine, and bromine at C-2 of purine nucleosides. Can. J. Chem. 1981, 2608) to give a mixture of 10–13, which was separated to the individual isomers 4 (24%), 5 (18.6%), 6 (25.8%) and 7 (16%). The guanine 8 and 2,6-diamino 9 derivatives were prepared by the treatment of 4 with 2-mercaptoethanol/NaOMe and ammonia in ethanol, respectively. The free nucleosides 10–15 were obtained upon treatment of the corresponding 5'-silylated nucleosides with n-$Bu_4$NF in good yields. The α-isomers 12 and 13 were prepared by the similar procedure as the β-isomers.

EXAMPLE 1

Preparation of Enantiomerically Pure β-D-Dioxolanyl Purine Nucleosides (2R,4R) and (2R,4S)-9-[[2-[(tert-Butyldiphenylsilyl) oxy]methyl]-1,3-dioxolan-4-yl]-6-chloro-2-fluoropurine (2 and 3).

A mixture of 2-fluoro-6-chloropurine (4.05 g, 23.47 mmol) and ammonium sulfate (catalytic amount) in hexamethyldisilazane (940 mL) was refluxed for 2 hours. The resulting solution was concentrated under anhydrous conditions to yield silylated 2-fluoro-6-chloropurine as a white solid. To a cooled (0° C.) and stirred solution of silylated 2-fluoro-6-chloropurine (5.69 g, 23.69 mmol) and compound 1 (7.84 g, 19.57 mmol) in dry methylene chloride (175 mL) was added TMSOTf (4.41 mL, 23.44 mmol). The reaction mixture was warmed to room temperature and stirred for 16 hours, during which time, all the initially formed $N_7$ condensed product was converted to $N_9$-isomer. The reaction mixture was quenched with saturated $NaHCO_3$ solution (50 mL) and stirred for an additional 20 minutes at room temperature, evaporated to dryness under reduced pressure. The residue was dissolved in ethyl acetate (200 mL), washed with water and brine, dried (anhydrous $Na_2SO_4$), filtered and evaporated to give a solid residue, which was purified by silica gel column chromatography (20% EtOAc in hexanes) to afford a mixture of β-anomer 8 and α-anomer 9 (1.3:1; β/α) as a white crystalline solid (6.30 g, 62.8%). The analytical sample was purified by preparative TLC using $CH_2Cl_2$-acetone (19:1) as the developing system to give 2 ($R_f$=0.50) and 3 ($R_f$=0.55) for NMR characterization: UV (MeOH) $\mu_{max}$ 269.0 nm.

(−)-(2R, 4R)-2-Amino-9-[[2-[(tert-butyldiphenylsilyl)oxy] methyl]-1,3-(dioxolan-4-yl]-6-chloropurine (4), (−)-(2R, 4R)-9-[[2-[(tert-Butyldiphenylsilyl) oxy]methyl]-1,3-dioxolan-4-yl]-2-fluoroadenine (5), (+)-(2R, 4S)-2-Amino-9-[[2-[(tert-2-[(tert-butyldiphenylsilyl) oxy]methyl]-1,3-dioxolan-4-yl ]-6-chloropurine (6) and (+)-(2R, 4S)-9-[[2-[ (tert-Butyldiphenylsilyl)oxy]methyl]-1,3-dioxolan -4-yl ]-2-fluoroadenine (7).

Dry ammonia gas was bubbled into a stirred solution of 2 and 3 (6.25 g, 12.18 mmol) in DME (125 mL) overnight). The solvent was evaporated under reduced pressure and the residue was subjected to chromatographic separation of the four compounds on a silica gel column (20–30% ethyl acetate in $CH_2Cl_2$). 4 ($R_f$=0.35, 1.49 g, 24%): a white crystalline solid. UV (MeOH) $\lambda_{max}$ 309.5 nm. Anal. ($C_{25}H_{28}ClN_5O_3Si$) C, H, Cl, N. 5 ($R_f$=0.21, 1.12 g, 18.6%): colorless needles. UV (MeOH) $\lambda_{max}$ 261.0, 268.0 (sh) nm. Anal. ($C_{25}H_{28}FN_5O_3Si$) C, H, F, N. 6 ($R_f$=0.43, 1.60 g, 25.76%): a white crystalline solid. UV (MeOH) $\lambda_{max}$ 261.0, 269.0 (sh) nm. Anal. ($C_{25}H_{28}FN_5O_3Si$) C, H, F, N. 7 ($R_f$=0.12, 0.96 g, 16%), a microcrystalline solid. UV (methanol) $\lambda_{max}$ 261.0, 269.0 (sh) nm. Anal. ($C_{25}H_{28}FN_5O_3Si$) C, H, F, N.

(−)-(2R,4R)-2-Amino-6-chloro-9-[(2-hydroxymethyl)-1,3-dioxolan-4-yl]purine (10).

A solution of 4 (0.46 g, 0.91 mmol) in THF (20 mL) was treated with 1M n-$Bu_4$NF/THF (1.1 mL, 1.1 mmol) to give 10 ($R_f$=0.50, 0.21 g, 84%) as a crystalline solid, which was recrystallized from MeOH: UV ($H_2O$) $\lambda_{max}$ 307.0 nm (ε8, 370) (pH7), 307.5 (ε8,590) (pH 2), 307.0 (ε8,800) (pH 11). Anal. ($C_9H_{10}ClN_5O_3$) C, H, Cl, N. (−)-(2R,4R)-2-Fluoro-9-[(2-hydroxymethyl)-1,3-dioxolan-4-yl]adenine (11).

A solution of 5 (0.56 g, 1.12 mmol) in THF (20 mL) was treated with 1 M n-$Bu_4$NF/THF (1.35 mL, 1.35 mmol) to furnish 22 (0.24 g, 85%) as a white crystalline solid, which was recrystallized from MeOH: UV ($H_2O$)$\lambda_{max}$ 260.8 run (817,010), 268.5 (sh) run (ε13,510) (.pH 7), 261.0 (ε16,390), 268.5 (sh) (ε13,300) (pH2), 260.8 (ε16,700), 268.5 (sh) (ε13,200) (pH 11). Anal. ($C_9H_{10}FN_5O_3$) C, H, F, N. (−)-(2R,4R)-9-[(2-hydroxymethyl)-1,3-dioxolan-4-yl]guanine (14).

A mixture of 4 (0.29 g, 0.57 mmol), $HSCH_2CH_2OH$ (0.51 mL) and 1.0 M NaOMe/MeOH (11.5 mL) in MeOH (20 mL) was refluxed for 3 hours. The reaction mixture was cooled and neutralized with glacial acetic acid. The solution was evaporated to dryness, and then the residue was triturated with $CHCl_3$, filtered and the filtrate was taken to dryness to give crude compound 8 (0.21 g, 75%), which without further purification was subjected to desilylation to give compound 3 (0.07 g, 61%) as a microcrystalline solid, which was recrystallized from MeOH: UV (H$_2$O) $\lambda_{max}$ 252.0 (ε8,730) (pH 7), 254.4 (ε12,130), 277.5 (sh) (ε8,070) (pH 2), 264.3 (ε10,800) (pH11). Anal. (C$_9$H$_{11}$N$_5$O$_4$) C, H, N. (−)-(2R,4R)-2-Amino-9-[(2-hydroxyethyl1)-1,3-dioxolan-4-yl]adenine (15).

A steel bomb was charged with compound 4 (0.28 g, 0.55 mmol), anhydrous ethanol (20 mL) saturated with NH$_3$, and heated at 90° C. for 6 hours. After cooling, the compound 9 (0.26 g, 95%) obtained on evaporated of the solvent in vacuo, and then desilylated according to the same procedure described for preparation of 12 to give 15 (0.10 g, 75%) as white micro needles, recrystallized from MeOH: UV (H$_2$O) $\lambda_{max}$ 279.0 nm (ε8,040) (pH 7), 290.0 (ε7,070) (pH 2), 278.8 (ε7,580) (pH 11). Anal. (C$_9$H$_{12}$N$_6$O$_3$) C, H, N.

(−)-(2R,4R)-2-Amino-9-[(2-hydroxymethyl)-1,3-dioxolan-4-yl]purine can be prepared by reduction of compound 10 using a variety of reducing agents, including palladium on carbon and hydrogen gas or tributyltin hydride and azabisisobutyronitrile.

II. Anti-HBV Activity of Dioxolane Nucleosides

The ability of β-D-dioxolane-nucleosides to inhibit HBV can be measured by various experimental techniques. The assay used herein to evaluate the ability of the disclosed compounds to inhibit the replication of HBV is described in detail in Korba and Gerin, Antiviral Res. 19:55–70 (1992). For purposes of illustration only, and without limiting the invention, below is provided the results of the evaluation of toxicity and anti-HBV activity of (−)-(2R,4R)-2-amino-6-chloro-9-[(2-hydroxymethyl )-1,3-dioxolan-4-yl]purine; (−)-(2R,4R)-2-amino-9-[(2-hydroxymethyl)-1,3-dioxolan-4-yl]adenine; and (−)-(2R,4R)-9-[(2-hydroxymethyl)-1,3-dioxolan-4-yl]guanine. The other compounds disclosed herein are evaluated similarly.

The antiviral evaluations were performed on two separate passages of cells, two cultures per passage (4 cultures total). All wells, in all plates, were seeded at the same density and at the same time.

Due to the inherent variations in the levels of both intracellular and extracellular HBV DNA, only depressions greater than 3.0-fold (for HBV virion DNA) or 2.5-fold (for HBV DNA replication intermediates) from the average levels for these HBV DNA forms in untreated cells are generally considered to be statistically significant [P<0.05] (Korba and Gerin, Antiviral Res. 19: 55–70, 1992). The levels of integrated HBV DNA in each cellular DNA preparation (which remain constant on a per cell basis in these experiments) were used to calculate the levels of intracellular HBV DNA forms, thereby eliminating technical variations inherent in the blot hybridization assays.

Typical values for extracellular HBV virion DNA in untreated cells range from 50 to 150 pg/ml culture medium (average of approximately 76 pg/ml). Intracellular HBV DNA replication intermediates in untreated cells range from 50 to 100 pg/ug cell DNA (average approximately 74 pg/ug cell DNA). In general, depressions in the levels of intracellular HBV DNA due to treatment with antiviral compounds are less pronounced, and occur more slowly, than depressions in the levels of HBV virion DNA.

For reference, the manner in which the hybridization analyses were performed for these experiments results in an equivalence of approximately 1.0 pg intracellular HBV DNA/ug cellular DNA to 2–3 genomic copies per cell and 1.0 pg of extracellular HBV DNA/ml culture medium to 3×10$^5$ viral particles/ml.

Toxicity analyses were performed in order to assess whether any observed antiviral effects are due to a general effect on cell viability. The method used was based on the uptake of neutral red dye, a standard and widely used assay for cell viability in a variety of virus-host systems, including HSV (herpes simplex virus) and HIV. Details of the procedure are provided in the toxicity table legends.

The test compounds were used in the form of 40 mM stock solutions in DMSO (frozen on dry ice). Daily aliquots of the test samples were made and frozen at −20° C. so that each individual aliquot would be subjected to a single freeze-thaw cycle. The daily test aliquots were thawed, suspended into culture medium at room temperature and immediately added to the cell cultures. The compounds were tested at 0.0 and 1 μM for antiviral activity. The compounds were tested for toxicity at concentrations up to 300 μM.

The following abbreviations are used in the Tables: ACPD, (−)-(2R,4R)-2-amino-6-chloro-9-[(2-hydroxymethyl)-1,3-dioxolan-4-yl]purine; DAPD, (−)-(2R,4R)-2-amino-9-[(2-hydroxymethyl)-1,3-dioxolan-4-yl]adenine; and Dioxolane-G, (−)-(2R,4R)-9-[(2-hydroxymethyl)-1,3-dioxolan-4-yl]guanine.

EXAMPLE 2

Toxicity of Compounds

The ability of the enantiomers of ACPD, DAPD, and dioxolane-G to inhibit the growth of virus in 2.2.15 cell cultures (HepG2 cells transformed with hepatitis virion) was evaluated. As illustrated in Table 1, no significant toxicity (greater than 50% depression of the dye uptake levels observed in untreated cells) was observed for any of the test compounds at the concentrations used for the antiviral evaluations. The test compounds were not toxic to 2.2.15 cells at 100 μM. The compounds were moderately toxic at 300 μM, however, all three compounds exhibited less toxicity at this conentration than ddC.

Toxicity analyses were performed in 96-well flat bottomed tissue culture plates. Cells for the toxicity analyses were cultured and treated with test compounds with the same schedule as used for the antiviral evaluations. Each compound was tested at 4 concentrations, each in triplicate cultures. Uptake of neutral red dye was used to determine the relative level of toxicity. The absorbance of internalized dye at 510 nM (A$_{510}$) was used for the quantitative analysis. Values are presented as a percentage of the average A$_{510}$ values (±standard deviations) in 9 separate cultures of untreated cells maintained on the same 96-well plate as the test compounds. The percentage of dye uptake in the 9 control cultures on plate 40 was 100±3. At 150–190 μM2', 3'-ddC, a 2-fold reduction in dye uptake (versus. the levels observed in untreated cultures) is typically observed in these assays (Korba and Gerin, Antiviral Res. 19: 55–70, 1992).

TABLE 1

Toxicity analysis of test compounds in 2.2.15 cells.

| PLATE | COMPOUND | NEUTRAL RED DYE UPTAKE AT INDICATED DRUG CONCENTRATION (% OF CONTROL) | | | |
|---|---|---|---|---|---|
| | | 1000 μM | 300 μM | 100 μM | 30 μM |
| 40 | 2',3'-ddC | 5 ± 1 | 44 ± 1 | 97 ± 2 | 101 ± 1 |

| PLATE | COMPOUND | NEUTRAL RED DYE UPTAKE AT INDICATED DRUG CONCENTRATION (% OF CONTROL) | | | |
|---|---|---|---|---|---|
| | | 300 μM | 100 μM | 30 μM | 10 μM |
| 40 | ACPD | 63 ± 1 | 99 ± 1 | 101 ± 2 | 98 ± 2 |

TABLE 1-continued

Toxicity analysis of test compounds in 2.2.15 cells.

| 40 | DAPD | 49 ± 3 | 88 ± 1 | 99 ± 3 | 99 ± 1 |
|---|---|---|---|---|---|
| 40 | Dioxolane-G | 56 ± 3 | 88 ± 3 | 101 ± 2 | 100 ± 3 |

EXAMPLE 3

Anti-Hepatitis B Virus Activity

As indicated in Table 2, within normal variations, levels of HBV virion DNA and intracellular HBV replication intermediates [HBV RI] remained constant in the untreated cells over the challenge period. The positive treatment control, 2',3'-dideoxycytosine [2',3'-ddC], induced significant depressions of HBV DNA replication at the concentration used. Previous studies have indicated that 9–12 µM 2',3'-ddC, a 90% depression of HBV RI (relative to average levels in untreated cells) is typically observed in this assay system (Korba and Gerin, Antiviral Res. 19: 55–70, 1992).

All three test compounds were potent inhibitors of HBV replication, causing depression of HBV virion DNA and HBV RI to a degree comparable to, or greater than, that observed following treatment with 2',3'-ddC.

TABLE 2

EFFECT OF VARIOUS NUCLEOSIDES ON HBV PRODUCTION IN 2.2.15 CELLS

| Treatment | | HBV virion DNA** pg/ml of cultured medium on day: | | | | Intracellular HBV on Day 10 pg/µM cellular DNA* | |
|---|---|---|---|---|---|---|---|
| | | 0 | 3 | 6 | 9 | Mono | RI |
| None | | 50 | 70 | 66 | 59 | 2.8 | 65 |
| | | 52 | 56 | 68 | 70 | 2.8 | 76 |
| | | 83 | 64 | 74 | 77 | 2.1 | 70 |
| | | 67 | 69 | 99 | 92 | 2.4 | 83 |
| | Mean | 63.00 | 64.75 | 76.75 | 74.50 | 2.53 | 73.50 |
| | S.D. | 15.34 | 6.40 | 15.22 | 13.82 | 0.34 | 7.77 |
| DDC 10 µM | | 66 | 50 | 20 | 2 | 0.9 | 6 |
| | | 58 | 52 | 13 | 3 | 1.0 | 4 |
| | | 67 | 51 | 19 | 2 | 1.4 | 5 |
| | | 51 | 48 | 17 | 2 | 1.1 | 7 |
| | Mean | 60.50 | 50.25 | 17.25 | 2.25 | 1.10 | 5.50 |
| | S.D. | 7.51 | 1.71 | 3.10 | 0.50 | 0.22 | 1.29 |
| | % inhibition | 3.97 | 22.39 | 77.52 | 96.98 | 56.44 | 92.52 |
| 1.0 µM (−)- -2-NH2-6-Cl- purine-dioxolane | | 71 | 56 | 27 | 6 | 0.8 | 9 |
| | | 56 | 52 | 21 | 3 | 0.8 | 14 |
| | | 57 | 65 | 20 | 2 | 1.1 | 10 |
| | | 69 | 70 | 16 | 5 | 1.2 | 11 |
| | Mean | 63.25 | 59.26 | 21.00 | 4.00 | 0.98 | 11.00 |
| | S.D. | 7.85 | 9.78 | 4.55 | 1.83 | 0.21 | 2.16 |
| | % inhibition | −0.40 | 8.49 | 72.64 | 94.63 | 61.39 | 85.03 |
| 0.1 µM (−)- -2-NH2-6-Cl purine-dioxolane | | 66 | 60 | 49 | 29 | 2.1 | 36 |
| | | 51 | 54 | 39 | 21 | 2.4 | 33 |
| | | 62 | 79 | 36 | 20 | 2.2 | 31 |
| | | 68 | 84 | 43 | 17 | 2.6 | 29 |
| | Mean | 61.75 | 69.25 | 41.75 | 21.75 | 2.33 | 32.25 |
| | S.D. | 7.59 | 14.50 | 5.62 | 5.12 | 0.22 | 2.99 |
| | % inhibition | 1.98 | −6.95 | 45.60 | 70.81 | 7.92 | 56.12 |
| 1.0 M (−)- -2,6-DiNH2- purine-dioxolane | | 66 | 59 | 12 | 0 | 1.2 | 3 |
| | | 70 | 45 | 10 | 1 | 1.4 | 3 |
| | | 74 | 56 | 15 | 0 | 0.9 | 1 |
| | | 61 | 43 | 11 | 0 | 1.1 | 2 |
| | Mean | 67.75 | 50.75 | 12.00 | 0.25 | 1.15 | 2.25 |
| | S.D. | 5.56 | 7.93 | 2.16 | 0.50 | 0.21 | 0.96 |
| | % inhibition | −7.54 | 21.62 | 84.36 | 99.66 | 54.46 | 96.94 |
| 0.1 µM (−)- -2,6-diNH2- purine-dioxolane | | 52 | 67 | 28 | 5 | 2.3 | 14 |
| | | 58 | 59 | 34 | 6 | 2.4 | 11 |
| | | 64 | 59 | 35 | 9 | 2.6 | 13 |
| | | 77 | 62 | 26 | 8 | 2.1 | 10 |
| | Mean | 62.75 | 61.75 | 30.75 | 7.00 | 2.35 | 12.00 |
| | S.D. | 10.69 | 3.77 | 4.43 | 1.83 | 0.21 | 1.83 |
| | % inhibition | 0.40 | 4.63 | 59.93 | 90.60 | 6.93 | 83.67 |
| 1.0 µM (−)- -2,6- dioxlane-G | | 70 | 86 | 22 | 2 | 2.0 | 6 |
| | | 50 | 59 | 24 | 4 | 1.9 | 6 |
| | | 56 | 56 | 23 | 2 | 1.4 | 3 |
| | | 73 | 62 | 20 | 3 | 2.1 | 4 |
| | Mean | 62.25 | 66.75 | 22.25 | 2.75 | 1.85 | 4.75 |
| | S.D. | 113.72 | 1.71 | 0.96 | 0.31 | 1.50 | |
| | % inhibition | 1.19 | −1.54 | 71.01 | 96.31 | 26.73 | 93.54 |
| 0.1 µM (−)- -2,6- dioxolane-G | | 51 | 77 | 60 | 18 | 2.0 | 28 |
| | | 59 | 62 | 70 | 12 | 2.2 | 23 |
| | | 74 | 73 | 69 | 14 | 2.8 | 25 |
| | | 67 | 61 | 82 | 11 | 2.4 | 20 |
| | Mean | 62.75 | 68.25 | 70.25 | 13.75 | 2.35 | 24.00 |
| | S.D. | 9.95 | 7.97 | 9.03 | 3.20 | 0.34 | 3.37 |
| | % inhibition | 0.40 | −5.41 | 8.47 | 81.54 | 6.93 | 67.35 |

*Analysis of intracellular HBV DNA was 24 hours following the 9th day of treatment.
DNA in each cell DNA preparation were used to calculate the levels of episomal 3.2 kB HBV genomes (MONO.) and HBV DNA replication intermediates [RI].
**A "zero" indicates an undetectable level of HBV DNA, sensitivity cutoff was 0.1 pg[m].

IV. Preparation of Pharmaceutical Compositions

The compounds disclosed herein and their pharmaceutically acceptable salts, prodrugs, and derivatives, are useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

Humans suffering from any of these conditions can be treated by administering to the patient an effective amount of (−)-(2R,4R)-2-amino-6-chloro-9-[(2-hydroxymethyl)-1,3-dioxolan-4-yl]purine; (−)-(2R,4R)-9-[(2-hydroxymethyl)-1,3-dioxolan-4-yl]guanine; (−)-(2R,4R)-2-amino-9-[(2-hydroxymethyl)-1,3-dioxolan-4-yl]adenine; or (−)-(2R,4R)-2-amino-9-[(2-hydroxymethyl )-1,3-dioxolan-4-yl]purine or a pharmaceutically acceptable derivative or salt thereof, optionally in a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount without causing serious toxic effects in the patient treated.

A preferred dose of the active compound for all of the above-mentioned conditions will be in the range from about 1 to 60 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art.

The compound is conveniently administered in unit any suitable dosage form, including but not limited to one containing 7 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.2 to 70 µM, preferably about 1.0 to 10 µM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like.

A syrup may contain, in addition to the active compounds, sucrose as a sweetening agent and certain preservatives, dyes and colorings and flavors.

The active compound, or pharmaceutically acceptable derivative or salt thereof can also be mixed with other active materials that do not impair the desired action, or with materials that supplement the desired action, such as antibiotics, antifungals, antiinflammatories, or other antivirals, including anti-HBV, anti-cytomegalovirus, or anti-HIV agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

V. Preparation of Phosphate Derivatives of β-D-Dioxolane-Nucleosides

Mono, di, and triphosphate derivative of β-D-dioxolane-nucleosides can be prepared as described below.

The monophosphate can be prepared according to the procedure of Imai et al., *J. Org. Chem.*, 34(6), 1547–1550 (June 1969). For example, about 100 mg of β-D-dioxolane-nucleoside and about 280 µl of phosphoryl chloride are reacted with stirring in about 8 ml of dry ethyl acetate at about 0° C. for about four hours. The reaction is quenched with ice. The aqueous phase is purified on an activated charcoal column, eluting with 5% ammonium hydroxide in a 1:1 mixture of ethanol and water. Evaporation of the eluant gives ammonium-(β-D-dioxolane-nucleoside)-5'-monophosphate.

The diphosphate can be prepared according to the procedure of Davisson et al., *J. Org. Chem.*, 52(9), 1794–1801 (1987). β-D-Dioxolane-nucleosides can be prepared from the corresponding tosylate, that can be prepared, for example, by reacting the nucleoside with tosyl chloride in pyridine at room temperature for about 24 hours, working up the product in the usual manner (e.g., by washing, drying, and crystallizing it).

The triphosphate can be prepared according to the procedure of Hoard et al., *J. Am. Chem. Soc.*, 87(8), 1785–1788 (1965). For example, β-D-dioxolane-nucleoside is activated (by making a imidazolide, according to methods known to those skilled in the art) and treating with tributyl ammonium pyrophosphate in DMF. The reaction gives primarily the triphosphate of the nucleoside, with some unreacted monophosphate and some diphosphate. Purification by anion exchange chromatography of a DEAE column is followed by isolation of the triphosphate, as the tetrasodium salt.

This invention has been described with reference to its preferred embodiments. Variations and modifications of the invention, enantiomerically pure β-D-dioxolane-nucleosides, will be obvious to those skilled in the art from the foregoing detailed description of the invention. It is intended that all of these variations and modifications be included within the scope of the appended claims.

I claim:

1. A method for the treatment of HBV infection in a human or other host animal, comprising administering an HBV treatment amount of the nucleoside of the formula:

wherein R is OH or NH$_2$, and X is selected from the group consisting of hydrogen, acyl, monophosphate, diphosphate, and triphosphate, or its pharmaceutically acceptable salt, and wherein the compound is at least 95% free of the corresponding β-L enantiomer in combination with a compound selected from the group consisting of 2-hydroxymethyl-5-(5-fluorocytosin-1-yl)-1,3-oxathiolane; 2-hydroxymethy-5-(cytosin-1-yl)-1,3-oxathiolane; carbovir, or interferon.

2. A method for the treatment of HBV infection in a human or other host animal, comprising administering an HBV treatment amount of the nucleoside of the formula:

wherein R is NH$_2$, and X is selected from the group consisting of hydrogen, acyl, monophosphate, diphosphate, and triphosphate, or its pharmaceutically acceptable salt, and wherein the compound is at least 95% free of the corresponding β-L enantiomer in combination with a compound selected from the group consisting of 2-hydroxymethyl-5-(5-fluorocytosin-1-yl)-1,3-oxathiolane; 2-hydroxymethyl-5-(cytosin-1-yl)-1,3-oxathiolane; carbovir, or interferon.

3. A method for the treatment of HBV infection in a human or other host animal, comprising administering an HBV treatment amount of the nucleoside of the formula:

wherein R is NH$_2$, H or Cl, and X is selected from the group consisting of hydrogen, acyl, monophosphate, diphosphate, and triphosphate, or its pharmaceutically acceptable salt, and Wherein the compound is at least 95% free of the corresponding β-L enantiomer in combination with a compound selected from the group consisting of 2-hydroxymethyl-5-(5-fluorocytosin-1-yl)-1,3-oxathiolane; 2-hydroxymethyl-5-(cytosin-1-yl)-1,3-oxathiolane; carbovir, or interferon.

4. A method for the treatment of HBV infection in a human or other host animal, comprising administering an HBV treatment amount of the nucleoside of the formula:

wherein R is OH or NH$_2$ and X is selected from the group consisting of hydrogen, acyl, monophosphate, diphosphate, and triphosphate, or its pharmaceutically acceptable salt in combination with a compound selected from the group consisting of 2-hydroxymethyl-5-(5-fluorocytosin-1-yl)-1,3-oxathiolane; 2-hydroxymethyl-5-(cytosin-1-yl)-I,3-oxathiolane; racemic carbovir, or interferon.

5. A method for the treatment of HBV infection in a human or other host animal, comprising administering an HBV treatment amount of the nucleoside of the formula:

wherein R is NH$_2$, and X is selected from the group consisting of hydrogen, acyl, monophosphate, diphosphate, and triphosphate, or its pharmaceutically acceptable salt in combination with a compound selected from the group consisting of 2-hydroxymethyl-5-(5-fluorocytosin-1-yl)-1, 3-oxathiolane; 2-hydroxymethyl-5-(cytosin-1-yl)-1,3-oxathiolane; carbovir, or interferon.

6. A method for the treatment of HBV infection in a human or other host animal, comprising administering an HBV treatment amount of the nucleoside of the formula:

wherein R is $NH_2$, H or Cl, and X is selected from the group consisting of hydrogen, acyl, monophosphate, diphosphate, and triphosphate, or its pharmaceutically acceptable salt in combination with a compound selected from the group consisting of 2-hydroxymethyl-5-(5-fluorocytosin-1-yl)-1,3-oxathiolane; 2-hydroxymethyl-5-(cytosin-1-yl)-1,3-oxathiolane; carbovir, or interferon.

7. The method of claim 1, wherein X is hydrogen.
8. The method of claim 1, wherein X is acyl.
9. The method of claim 1, wherein X is monophosphate.
10. The method of claim 1, wherein X is diphosphate.
11. The method of claim 1, wherein X is triphosphate.
12. The method of claim 2, wherein X is hydrogen.
13. The method of claim 2, wherein X is acyl.
14. The method of claim 2, wherein X is monophosphate.
15. The method of claim 2, wherein X is diphosphate.
16. The method of claim 2, wherein X is triphosphate.
17. The method of claim 3, wherein X is hydrogen.
18. The method of claim 3, wherein X is acyl.
19. The method of claim 3, wherein X is monophosphate.
20. The method of claim 3, wherein X is diphosphate.
21. The method of claim 3, wherein X is triphosphate.
22. The method of claim 4, wherein X is hydrogen.
23. The method of claim 4, wherein X is acyl.
24. The method of claim 4, wherein X is monophosphate.
25. The method of claim 4, wherein X is diphosphate.
26. The method of claim 4, wherein X is triphosphate.
27. The method of claim 5, wherein X is hydrogen.
28. The method of claim 5, wherein X is acyl.
29. The method of claim 5, wherein X is monophosphate.
30. The method of claim 5, wherein X is diphosphate.
31. The method of claim 5, wherein X is triphosphate.
32. The method of claim 6, wherein X is hydrogen.
33. The method of claim 6, wherein X is acyl.
34. The method of claim 6, wherein X is monophosphate.
35. The method of claim 6, wherein X is diphosphate.
36. The method of claim 6, wherein X is triphosphate.
37. The method of claim 3, wherein R=H.
38. The method of claim 3, wherein R=Cl.
39. The method of claim 6, wherein R=H.
40. The method of claim 6, wherein R=Cl.

* * * * *